United States Patent [19]

Pitts

[11] 4,386,932
[45] Jun. 7, 1983

[54] ABSORBENT ARTICLE

[76] Inventor: Linda F. Pitts, 196 Cherokee Rd., Asheville, N.C. 28804

[21] Appl. No.: 313,298

[22] Filed: Oct. 21, 1981

[51] Int. Cl.³ ............................................. A61F 13/16
[52] U.S. Cl. .................................................. 604/383
[58] Field of Search .............. 604/358, 378, 381, 385, 604/397, 383; 128/157–162, 168

[56] References Cited

U.S. PATENT DOCUMENTS 3,225,765 12/1965 Mosier et al. ....................... 604/397
3,945,386 3/1976 Anczurowski et al. ............. 604/383
3,965,906 6/1976 Karami .............................. 604/383
4,014,044 3/1977 Figueroa et al. ................... 128/168

Primary Examiner—C. Fred Rosenbaum
Attorney, Agent, or Firm—David M. Carter

[57] ABSTRACT

There is provided an improved sanitary napkin which utilizes a sheet metal substrate. The sheet metal substrate acts as a barrier to liquid flow. However, it includes a plurality of embossments having small holes therein which permit the sanitary napkin to breathe while also serving as a heat sink. The sanitary napkin also includes fluid absorbent layers overlying the sheet metal substrate.

9 Claims, 3 Drawing Figures

ABSORBENT ARTICLE

BACKGROUND OF THE INVENTION

This invention relates to an improved absorbent article. More particularly, it relates to an improved breathable sanitary napkin utilizing cotton absorbent layers for absorbing fluids during the female menstrual cycle.

Many of the prior art napkins include a thin plastic sheet on the bottom as a final barrier to prevent fluids from leaking onto clothing. An example of this type of napkin is shown in U.S. Pat. No. 3,897,782. One of the major problems with this type napkin is discomfort caused by sweating due to the fact that a thin plastic layer is impermeable to air and moisture. Various attempts have been made to alleviate the need for this plastic membrane.

One such technique is shown in U.S. Pat. No. 3,088,463, which shows a sanitary napkin having a layer including a plurality of holes therein for dispersing the fluid throughout the cotton absorbent material so that a pool of fluid is not readily formed. Another dispersion technique is shown in U.S. Pat. No. 3,375,827, which shows a waffling layer to provide for such dispersion. The techniques of dispersion have not met with good results in that the use of a plastic layer is still common.

OBJECT OF THE INVENTION

It is therefore one object of this invention to provide an improved sanitary napkin which is both comfortable and provides an adequate barrier to fluids.

It is another object to provide an improved sanitary napkin which both reduces sweating due to lack of breathability and further removes heat from the area.

It is still another object of the invention to provide a sanitary napkin of simplified construction which is effective.

SUMMARY OF THE INVENTION

In accordance with one form of this invention there is provided an improved sanitary napkin having a layer of fluid absorbent material. A metal sheet is provided having at least one embossment therein. Portions of the metal sheet are adjacent to the absorbent layer. At least one hole is provided through the embossment. The absorbent layer is positioned between the human body and the metal sheet. The sanitary napkin is thus breathable without a high risk of the penetration of menstrual fluids completely through the napkin.

BRIEF DESCRIPTION OF THE DRAWINGS

The subject matter which is regarded as the invention is set forth in the appended claims. The invention, however, together with further objects and advantages thereof may be better understood in reference to the accompanying drawing in which:

DESCRIPTION OF THE PREFERRED EMBODIMENT

Figure 1:
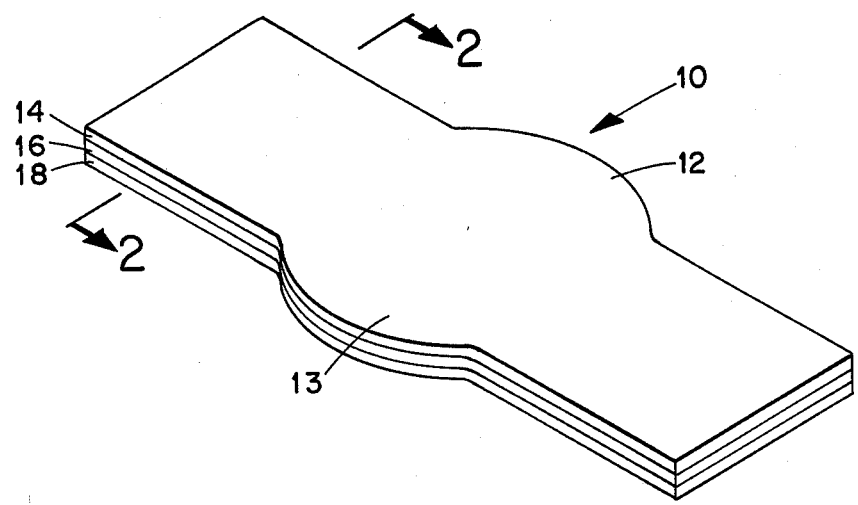
FIG. 1 is a pictorial view of the sanitary napkin of the subject invention.

Referring now more particularly to FIG. 1, there is provided sanitary napkin 10 in a generally elongated shape. The napkin includes side extensions 12 and 13 to provide comfort for the wearer. The napkin of the preferred embodiment includes three layers. The top layer 14, which contacts the human body, is the most absorbent layer and is generally made of thick cotton. Intermediate layer 16 is made of gauze and layer 18 is a thin metal sheet normally made of aluminum.

Figure 2:
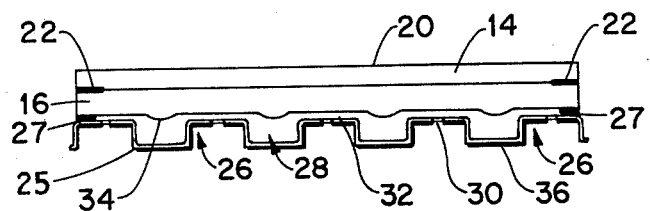
FIG. 2 is a sectional view taken along lines 2—2 of FIG. 1.

The construction of the layers of the napkin are more readily seen in reference to FIG. 2. As can be seen, cotton absorbent layer 14 contacts the fluids first from the human body at its top portion 20. This cotton layer absorbs most of the fluids. However, quite often some of the fluids will reach into gauze layer 16. Cotton layer 14 and gauze layer 16 are held together along their edges by means of glue strip 22. At the bottom of the construction is thin aluminum sheet 24 made of a plurality of embossments 26 and wells 28. There is a well between each adjacent embossment. The aluminum layer is held to the gauze layer by means of glue strip 28 along their respective edges. Each embossment 26 includes at least one hole 30 at the top 32 of the embossment. These holes 30 permit the napkin to breathe, that is, to permit relatively dry air to flow through the napkin from the outside to the human body and moisture laden air to flow from the human body through the napkin to the outside. However, these holes are small enough, e.g., less than ¼", so that large drops of fluids which may gather near the holes would not tend to penetrate there through. As can be seen from FIG. 2, the gauze layer tends to dip into wells 28, as shown in somewhat of an exaggerated fashion as dips 34. In the event that any fluids penetrate through cotton layer 14 and onto gauze layer 16, this fluid will travel by capillary action to these dips 34, and if sufficient fluids arrive in these areas, they will be deposited in the bottoms 36 of the wells 28. Thus the gauze layer will tend to conduct fluid away from holes 30 by capillary and gravity action. This ensures that fluids will not be deposited on the clothing of a female which will be in contact with the outside portion of the bottoms of the wells 36. Thus this gauze layer 16 acts as a regulator of fluid flow and the aluminum sheeting acts as a final barrier to fluid flow but permits the overall napkin to breathe because of the existence of holes 30.

Figure 3:
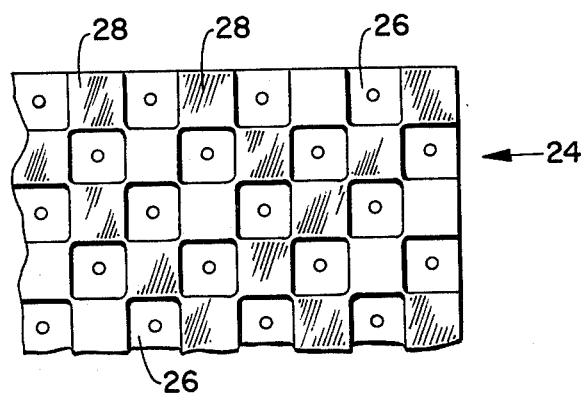
FIG. 3 is a partial plan view of the metal sheet shown in FIG. 2.

A partial plan view of aluminum sheeting 24 is seen in reference to FIG. 3. As can be seen, the sheeting is a matrix made up of alternating wells 28, shown shaded, and embossments 26, with the embossments having the breathing holes there through. The aluminum sheeting is made of a very thin flexible material so that the overall napkin is lightweight. Since the aluminum sheet is metal, it will conduct heat away from the human body, thus further alleviating the discomfort which occurred due to sweating in the prior art sanitary napkin.

To be more specific, the aluminum sheet is a final barrier for the body fluids. Most of the time there will be a convection action or relationship between the body fluids and the aluminum shield, since this metal shield will generally have lower temperature than the discharged body fluids. This lower temperature would also produce limited coagulation of body fluids producing an improved control of excess body fluids.

From the foregoing description of the illustrative embodiment of this invention it will be apparent that many modifications may be made therein. It will be understood, therefore, that this embodiment of the invention is intended as an exemplification of the invention only and that the invention is not limited thereto. It is to be understood that it is intended in the appended claims to cover all such modifications that shall fall within the true spirit and scope of the invention.

I claim:

1. An improved sanitary napkin comprising:
a first layer of fluid-absorbent material, a metal sheet, portions of said metal sheet are attached to and adjacent to said absorbent layer, said metal sheet having at least one embossment therein, at least one hole through said embossment; at least one well in said metal sheet located near said embossment, said well adapted to collect bodily fluids should said fluids penetrate through said first layer of fluid-absorbent material; when said napkin is worn said fluid-absorbent layer is positioned between the human body and said metal sheet whereby said napkin is breathable without high risk of the penetration of menstrual fluids completely through said napkin.

2. An sanitary napkin as set forth in claim 1, further including a plurality of embossments in said metal sheet, substantially all said embossments having at least one hole therein.

3. A sanitary napkin as set forth in claim 1, further including a second layer of absorbent material, said second layer adapted to absorb more fluid than said first layer, said first layer being between said second layer and said metal sheet.

4. A sanitary napkin as set forth in claim 3, wherein said first layer is gauze and said second layer is cotton.

5. A sanitary napkin as set forth in claim 1, wherein said sheet metal is aluminum.

6. A sanitary napkin as set forth in claim 2, further including a plurality of wells located between each embossment, said wells adapted to collect bodily fluids should said fluids penetrate through said first layer of fluid absorbent material.

7. A sanitary napkin as set forth in claim 6, wherein said wells include absorbent material therein.

8. An improved sanitary napkin comprising:
a first layer of fluid absorbent material, said first layer being gauze, a metal sheet having a plurality of embossments, a plurality of wells each located between adjacent embossments, said first layer of fluid absorbent material adjacent to the tops of said embossments and overlying the tops of said wells, at least one hole through the top of each embossment; a second layer of absorbent material situated above said first layer.

9. A sanitary napkin as set forth in claim 8, wherein portions of said first layer of fluid absorbent material extend into said wells.

* * * * *